United States Patent [19]
Meisterling

[11] Patent Number: 5,461,923
[45] Date of Patent: Oct. 31, 1995

[54] ACOUSTIC TRANSDUCER, TRANSDUCERIZED FASTENER AND METHOD OF MANUFACTURE

[75] Inventor: Jesse R. Meisterling, East Hampton, Conn.

[73] Assignee: Raymond Engineering Inc., Middletown, Conn.

[21] Appl. No.: 243,629

[22] Filed: May 16, 1994

[51] Int. Cl.⁶ .................................................. F16B 31/02
[52] U.S. Cl. ...................................... 73/761; 73/597
[58] Field of Search ............................. 73/581, 597, 761

[56] References Cited

U.S. PATENT DOCUMENTS

| | | |
|---|---|---|
| 3,759,090 | 9/1973 | McFaul et al. . |
| 3,810,385 | 5/1974 | McFaul et al. . |
| 4,294,122 | 10/1981 | Couchman . |
| 4,295,377 | 10/1981 | Couchman . |
| 4,413,518 | 11/1983 | Jones . |
| 4,601,207 | 7/1986 | Steblay ........................... 73/761 |
| 4,676,109 | 6/1987 | Wallace ........................... 73/761 |
| 4,686,859 | 8/1987 | Wallace ........................... 73/761 |
| 4,760,740 | 8/1988 | Meisterling ..................... 73/761 |
| 4,846,001 | 7/1989 | Kibblewhite . |
| 4,899,591 | 2/1990 | Kibblewhite . |
| 5,112,248 | 5/1992 | Kibblewhite et al. ........... 73/761 |
| 5,131,276 | 7/1992 | Kibblewhite ................... 73/761 |
| 5,220,839 | 6/1993 | Kibblewhite ................... 73/761 |
| 5,291,789 | 3/1994 | Walton ........................... 73/761 |

*Primary Examiner*—Richard E. Chilcot, Jr.
*Assistant Examiner*—Eric S. McCall
*Attorney, Agent, or Firm*—Fishman, Dionne & Cantor

[57] ABSTRACT

An improved acoustic transducer, transducerized fastener and method of manufacture are presented wherein a piezoelectric crystal and a contact/retaining button assembly are permanently attached to a fastener. The contact/retaining button assembly has an insulator board sandwiched between upper and lower electrodes, with at least one plated thru-hole for electrical contact between the electrodes.

17 Claims, 1 Drawing Sheet

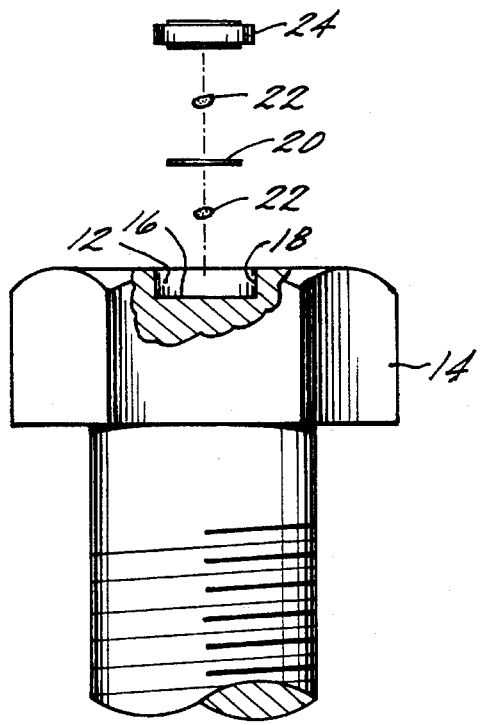
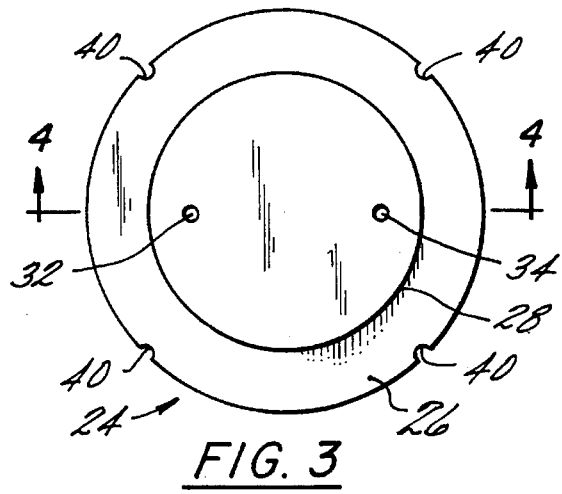
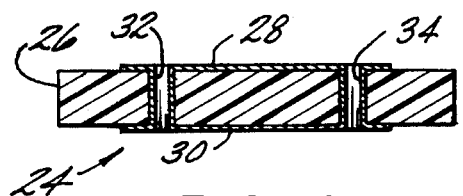
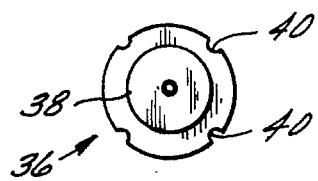
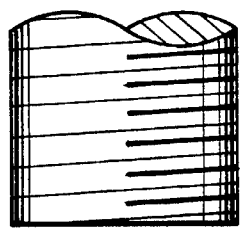
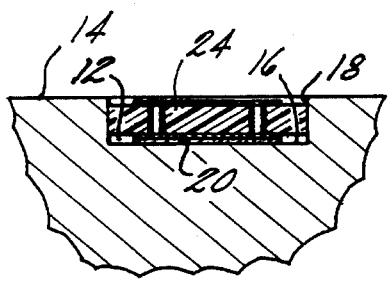
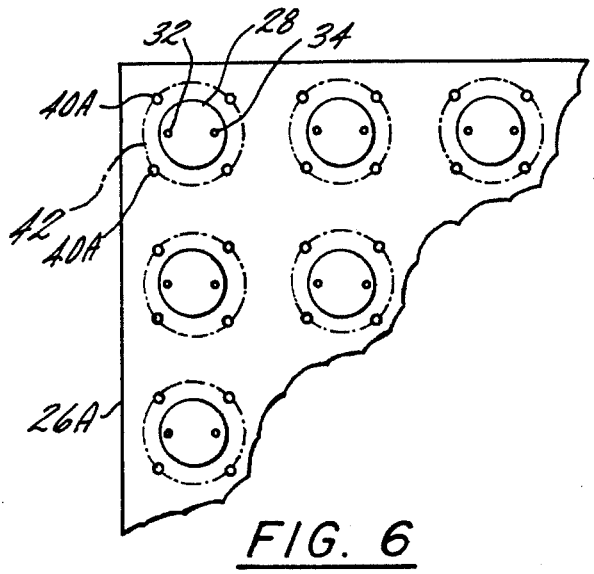

ACOUSTIC TRANSDUCER, TRANSDUCERIZED FASTENER AND METHOD OF MANUFACTURE

BACKGROUND OF THE INVENTION

This invention relates to the field of ultrasonic measurement of a load or strain in a fastener member. More particularly, this invention relates to an ultrasonic transducer which is intended to be fixed on a fastener, and the resulting fastener.

The theory and use of ultrasonic techniques for measuring the load or strain in a fastener, such as a bolt, and apparatus therefor are well known in the art. See, for example, the patents to McFaul et al 3,759,090, McFaul 3,810,385, and Jones 4,413,518, the entire disclosures of all of said patents being incorporated herein by reference. The technique of ultrasonic measurement of load in a fastener involves the mounting of a piezoelectric ultrasonic transducer on the fastener to propagate ultrasonic waves in the fastener. Prior patents teach that the transducer can be removeably mounted on the fastener or contained in the head of a fastening tool, and a coupling medium, such as a coupling oil is used between the transducer and the fastener. Proposals have also been made to permanently mount the ultrasonic transducer on the fastener. See, e.g., U.S. Pat. Nos. 4,294,122 and 4,295,377 to Couchman and U.S. Pat. Nos. 4,846,001 and 4,899,591 to Kibblewhite, the entire disclosures of all of said patents being incorporated herein by reference.

SUMMARY OF THE INVENTION

The present invention relates to an improved ultrasonic transducer, an improved transducerized fastener, and a method of manufacture of the improved transducer and transducerized fastener.

In accordance with the present invention, the transducer is permanently mounted on the fastener. As used in conjunction with this invention, permanent mounting means that the transducer is attached to the fastener by an adhesive or the like to effect a relatively long term attachment. However, it should be understood that the concept of permanent mounting contemplates situations where the transducer could be removed and replaced by another transducer for further long term attachment, as distinguished from mounting the transducer on the fastener for each measurement operation. Also, although the present invention will be described with reference to a bolt, and to a transducer mounted on the head of the bolt, it should be understood that other fasteners may be used and that the transducer may be mounted on any end of the fastener.

In the present invention, a piezoelectric crystal is bonded to the head of a bolt, preferably in a recess at the head of the bolt. A contact/retaining button is bonded to the piezoelectric crystal. The contact/retaining button includes a printed circuit (PC) board-like material with thin electrodes on opposed upper and lower surfaces of the PC board. The upper and lower electrodes are electrically connected by at least one plated thru-hole extending through the PC board. The electrical signal for ultrasonic transducer operation is delivered to the upper electrode, and via the plated thru-hole to the lower electrode. Capacitive coupling between the lower electrode and the ultrasonic transducer excites the transducer to produce the ultrasonic signal which travels along the length of the bolt for ultrasonic measurement of the load or strain in the bolt. A plurality of vent holes formed around the perimeter of the PC board provide a vent for the adhesive and enable centering of the crystal in the recess.

BRIEF DESCRIPTION OF THE DRAWINGS

Referring to the drawings, wherein like elements are numbered alike in the several FIGURES:

FIG. 1 is a partial sectional elevation view of a bolt, the piezoelectric crystal and contact/retaining button of this invention shown in an exploded view.

FIG. 2 is a detail of FIG. 1 showing in section an assembly of the piezoelectric crystal and contact/retaining button mounted in the head of the bolt.

FIG. 3 is an enlarged top plan view of the contact/retaining button of FIGS. 1 and 2.

FIG. 4 is a sectional elevation view of the contact/retaining button of FIG. 3.

FIG. 5 is a top plan view of another embodiment of a contact/retaining button.

FIG. 6 is a top plan view of an array of contact/retaining buttons before singulation.

DESCRIPTION OF THE PREFERRED EMBODIMENT

Referring to FIGS. 1 and 2, a bolt 10 has a cylindrical recess 12 of circular cross section formed in the head 14 of the bolt. Recess 12 has a bottom or floor 16 and a circular sidewall 18. A piezoelectric crystal 20 is bonded to floor 16 of the recess by an adhesive 22. The piezoelectric crystal is preferably a 5 MHz EBL2 available from Stavley Sensors Inc. of East Hanford, Conn., and the adhesive is preferably a high temperature epoxy adhesive, such as EP65HT-1 available from Master Bond of Teaneck, N.J.

A contact/retaining button 24 is bonded to the top surface of piezoelectric crystal 20, also by the same high temperature epoxy adhesive which bonds the lower surface of the crystal to the floor of recess 12. Contact/retaining button 24 has a thin central layer of rigid PC board material 26, such as fiberglass reinforced epoxy board or polyimide board suitable for high temperature applications, and contact/retaining button 24 has an overall diameter just slightly less than the diameter of recess 12 (e.g., about 0.005 less). Circular copper discs 28 and 30 are bonded or otherwise secured to the opposite faces of board 26. Plated thru-holes 32 and 34, i.e., through holes in board 26 plated with copper, establish electrical contact between upper copper disc 28 and lower copper disc 30. The thru-holes are formed by any technique known in the printed circuit art (e.g., drilling, laser ablation), and the thru-holes are plated with copper by any technique known in the printed circuit art. While two plated thru-holes are shown in the embodiment of FIGS. 3 and 4, it should be understood that a single plated thru-hole will suffice, or a solid conductive rod could be used as long as electrical contact is established between upper disc 28 and lower disc 30.

A plurality of vent holes 40 is formed at four locations spaced 90° apart on the periphery of circular board 26. These vent holes serve to vent the epoxy adhesive and facilitate centering of retainer button 24 when mounted in recess 12 of bolt 10.

The contact/retaining button shown in FIGS. 3 and 4 has typical dimensions of 0.060 inches for the height of board 26, a diameter of 0.375 inches for board 24, 10 mils (0.010 inches) for the thickness of each layer of copper, and a diameter of 0.250 inches. A typical button 34 of smaller diameter is shown in FIG. 5, wherein the board thickness would be 0.032 inches, the board diameter would be 0.125 inches, the upper and lower copper discs would be 10 mils (0.010 inches) thick and have a diameter of 0.115 inches. Note that in the embodiment of FIG. 5, the contact/retaining button 36 has a single central plated thru-hole 38 to establish electrical contact between the upper and lower copper discs on the contact/retaining button.

The contact/retainer buttons are formed by printed circuit techniques. Starting with a master rigid PC board 26A coated with copper on the opposed surfaces, a plurality of copper discs 28 and 30 are formed in pairs at directly opposed sites on the rigid board by conventional printed circuit techniques, e.g., photopatterning and etching. FIG. 6 shows a segment of such a board, with a plurality of individual discs 28 formed on one surface thereof. It should be clear and understood that the pattern for discs 28 is repeated for discs 30 at directly opposed sites on the bottom of board 26, and the plated thru-holes 32 and 34 are also formed when the buttons are in this multiple array format. Four holes 40A at 90° spacing are also drilled about each disc 28. The holes 40A are located so as to straddle the eventual outer diameter of the individual board segments 26, shown in dashed lines 42, intended to be formed from master board 26A. The individual contact/retaining buttons are singulated from master board 26A by being cut therefrom by any known method, such as by routing. The cut passes through the approximate center of each of the four holes 40A associated with each contact/retaining button, so that the vent holes 40 are formed and are present in the singulated retaining discs when they are cut from master board 26A.

After a retainer button and piezoelectric crystal are permanently secured in a recess 12 in the head of a bolt, ultrasonic measurement of the load or strain can be repeatedly effected by bringing the measuring instrument and probe into contact with upper copper disc 28. The electrical signal delivered to disc 28 is conducted to lower disc 30 via the plated thru-holes, and the signal is then capacitively coupled between lower disc 30 and piezoelectric crystal 20 to generate the ultrasonic signal that traverses the bolt. The return measurement signal is capacitively coupled between crystal 20 to lower copper disc 30, and is transmitted to the measuring instrument via the thru-holes and upper copper disc 28.

While this invention has been described in an embodiment wherein the piezoelectric crystal and contact/retaining button are located in a recess in the head of a bolt, the crystal and contact/retaining button could also be permanently mounted atop the head of a bolt without a recess, or they could also be mounted at the end of the bolt remote from the head if that remote end is accessible for measuring purposes. Also, it should be understood that although insulating material 26 has been described as rigid material, it may also be flexible insulating material, and the term "board" encompasses both rigid and flexible materials.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. A fastener adapted for load measurement including:

a fastener having first and second ends;

a piezoelectric element permanently mounted on one end of said fastener; and contact means permanently attached to said piezoelectric element, said contact means including:

a layer of insulating material having first and second opposed sides;

a first electrode on said first side of said insulating material, a second electrode on said second side of said insulating material;

one of said first and second electrodes being bonded to said piezoelectric element; and connecting means to establish electrical contact between said first and second electrodes.

2. A fastener as in claim 1 wherein:

said connecting means to establish electrical contact includes at least one thru-hole in said insulating material and electrically conductive material in said thru-hole extending between and contacting said first and second electrodes.

3. A fastener as in claim 1, wherein:

said layer of insulating material has an edge periphery, and further including:

vent means at the periphery of said layer of insulating material.

4. A fastener as in claim 1 wherein:

said contact means is a printed circuit element having first and second layers of conductive material on opposed sides of an insulating board.

5. A fastener adapted for load measurement including:

a fastener having first and second ends;

a recess in one end of said fastener;

a piezoelectric element permanently mounted in said recess in said fastener; and contact means in said recess permanently attached to said piezoelectric element, said contact means including:

a layer of insulating material having first and second opposed sides;

a first electrode on said first side of said insulating material, a second electrode on said second side of said insulating material;

one of said first and second electrodes being bonded to said piezoelectric element; and connecting means to establish electrical contact between said first and second electrodes.

6. A fastener as in claim 5 wherein:

said connecting means to establish electrical contact includes at least one thru-hole in said insulating material and electrically conductive material in said thru-hole extending between and contacting said first and second electrodes.

7. A fastener as in claim 5, wherein:

said layer of insulating material has an edge periphery, and further including:

vent means at the periphery of said layer of insulating material.

8. A fastener as in claim 5 wherein:

said contact means is a printed circuit element having first and second layers of conductive material on opposed sides of an insulating board.

9. A fastener as in claim 5 wherein:

said recess is circular in cross-section and is generally cylindrical;

said piezoelectric element is circular in cross-section; and said contact means is circular in cross-section.

10. A fastener as in claim 5 wherein:

said layer of insulating material has an edge periphery, and further including:

vent means at the periphery of said contact means.

11. A method of making a fastener adapted for load measurement, including the steps of:

forming a contact element having a layer of insulating material, first and second electrodes on opposed surfaces of said insulating material, and connecting means to establish electrical contact between said first and second electrodes;

forming a recess in one end of a fastener;

placing a piezoelectric element in said recess and permanently attaching said piezoelectric element to said fastener; and placing said contact element in said recess and permanently attaching said contact element to said piezoelectric element.

12. The method of claim 11 wherein:

each of said recess, said piezoelectric element and said contact element are of circular shape.

13. A method of claim 11 wherein:

said contact element has an edge periphery, and further including:

the step of forming a plurality of vents at the periphery of said contact element.

14. The method of claim 11 wherein:

each of said recess, said piezoelectric element and said contact element are of circular shape.

15. A method of making a contact element including the steps of:

defining first and second patterns of electrode elements on opposed sides of a master board of insulating material;

each of said electrodes on one side of said board being paired with an electrode on the opposed side of the board to form a paired set of electrodes;

establishing a path of electrical conductivity between each electrode and the electrode paired therewith;

forming a plurality of holes in said board;

at least one of each of said holes being associated with each pair of electrodes and being located at a position intended to be at the periphery of the contact element being made; and separating each paired set of electrodes and the board material therebetween from said master board, the location of separation of each paired set of electrodes passing thru said at least one hole associated with said paired set to establish a periphery of the board material and the paired set of electrodes with at least one vent hole at the periphery of the board material and said paired set of electrodes.

16. The method of making a contact element as in claim 15 wherein:

said step of forming a plurality of holes in said board includes forming a plurality of holes associated with each paired set of electrodes at positions intended to be at the periphery of the contact element being formed; and the location of separation of each paired set of electrodes passes through each of said plurality of holes associated with each paired set of electrodes to form a periphery of the board material and the paired set of electrodes with a plurality of vent holes at the periphery of the board material and said paired set of electrodes.

17. The method of making a contact element as in claim 16 wherein:

said plurality of vent holes associated with each paired set of electrodes is equally spaced about the periphery of the contact element.

* * * * *